United States Patent [19]

Mashelkar et al.

[11] Patent Number: 5,780,578

[45] Date of Patent: Jul. 14, 1998

[54] SYNTHETIC POLYMER EXHIBITING HYDROLYTIC ACTIVITY, ITS PREPARATION AND USE FOR CONVERSION OF ESTERS AND AMIDES TO THE CORRESPONDING ALCOHOL AND AMINE

[75] Inventors: Raghunath Anant Mashelkar; Mohan Gopalkishna Kulkarni; Rohini Nitin Karmalkar, all of Maharashtra, India

[73] Assignee: Council Of Scientific & Industrial Research, New Delhi, India

[21] Appl. No.: 616,094

[22] Filed: Mar. 14, 1996

[30] Foreign Application Priority Data

Jun. 14, 1995 [IN] India .................. 1094/Del/95
Jun. 14, 1995 [IN] India .................. 1095/Del/95

[51] Int. Cl.$^6$ .................. C08G 73/18; C08G 69/44
[52] U.S. Cl. .................. 528/327; 528/272; 528/289; 528/292; 528/310; 528/322; 528/328; 528/331; 528/347; 528/363
[58] Field of Search .................. 528/328, 272, 528/289, 310, 322, 363, 292, 327, 331, 347

[56] References Cited

PUBLICATIONS

Axen, R., & Emback, S., *Eur. J. Biochem.* 18:351 (1971), the month of publication is not available.

Breslow, R. *Science* 218:532 (1982), the month of publication is not available.

*Dahl, P.K., Sankar, Vidya Sankar, S., and Arnold, F.H., *Chem. Mater.* 7:154 (1995), the month of publication is not available.

D'Souza, V.T., Hanabusa, K., O'Leavy, T., Gadwood, R.C., and Bender, M.L., *Biochem. Biophys. Res. Commun.* 129:727 (1988), the month of publication is not available.

Koch–Schmidt, A.C., & Mosbach, K., *Biochemistry* 2105 (1977), the month of publication is not available.

Kumakura, M., & Kaetsu, I., *Coll. Czech. Chem. Commun.* 49:1552 (1984), the month of publication is not available.

Lehn, J.M. *Agnew, Chem. Int. Ed. Engl.* 27:90 (1988), the month of publication is not available.

*Leonhardt, A., and Mosbach, K., *React. Polym.* 6:285–287 (1987), the month of publication is not available.

Robinson, D.K., and Mosbach, K., *J. Chem. Soc. Chem. Commun.* 969 (1989), the month of publication is not available.

Sellergren, B., and Shea, K.J., *Tetrahedrom:Asymm.* 5:1403 (1994), the month of publication is not available.

Svec, F., Coupek, J., and Kalal, J., *Angew Makromol. Chem.* 48:135 (1975), the month of publication is not available.

Van den Berg, H.J., and Challa, G., in *Syntheses and Separation Using Functional Polymers*, p. 227, D.C. Sherrington and P. Hodge, (eds.), John Wiley and Sons, Chichester (1988), the month of publication is not available.

*Primary Examiner*—P. Hampton-Hightower
*Attorney, Agent, or Firm*—Merchant, Gould, Smith, Edell, Welter & Schmidt, P.A.

[57] ABSTRACT

The invention provides a polymer composed of vinyl monomers bearing imidazole, hydroxyl and carboxyl groups arranged in proximity to each other, that exhibits hydrolytic activity similar to serine proteases, and a process for its preparation. The polymer is useful for the hydrolysis of esters and amides to the corresponding alcohols and amines.

29 Claims, 2 Drawing Sheets

SYNTHETIC POLYMER EXHIBITING HYDROLYTIC ACTIVITY, ITS PREPARATION AND USE FOR CONVERSION OF ESTERS AND AMIDES TO THE CORRESPONDING ALCOHOL AND AMINE

FIELD OF THE INVENTION

The present invention relates to a new polymer composition that is useful for the conversion of esters and amides to the corresponding alcohols and amines, and a process for its preparation.

BACKGROUND OF THE INVENTION

Catalytic activity of hydrolytic enzymes in the hydrolysis of esters and amides is characterized by high reaction rates and high selectivity. However, they undergo irreversible deactivation at temperatures in the range of 40°–80° C., under very acidic (pH 1–2) or alkaline pH (pH 9–11), shear and in the presence of solvents. Since the enzymes are expensive, it is desirable to use them for repeated applications. But this is rendered difficult as the enzymes often lose their catalytic activity during their recovery from the reaction media. These disadvantages limit their industrial applications.

One way to get around this problem is to immobilize the enzymes on suitable polymeric supports (R. Axen & S. Ernback. *Eur. J. Biochem.* 18:351 (1971); A. C. Koch-Schmidt & K. Mosbach, *Biochemistry* 16:2015 (1977); M. Kumakura & I. Kaetsu, *Coll. Czech. Chem. Commun.* 49:1552 (1984)). These approaches however, cannot completely overcome the limitations of the enzymes. Also, the efficacy is limited by the extent of immobilization that could be achieved.

Publications in this area describe polymers that in solution act as catalysts for the hydrolysis of esters and amides (R. Breslow, *Science* 218:532 (1982); J. M. Lehn, *Angew. Chem. Int. Ed. Engl.* 27:90 (1988); V. T. D'Souza, K. Hanabusa, T. O'Leavy, R. C. Gadwood and M. L. Bender, *Biochem. Biophys. Res. Commun.* 129:727 (1988); H. J. Van den Berg and G. Challa, in *Syntheses and Separations Using Functional Polymers*, page 227, D. C. Sherrington and P. Hodge, (eds.), John Wiley and Sons, Chichester (1988)). Unfortunately, these polymers have very low activity and are difficult to recover from the reaction system.

Highly crosslinked polymers have also been used as catalysts for hydrolysis (A. Leonhardt and K. Mosbach., *React. Polym.* 6:285 (1987); B. Sellergren and K. J. Shea, *Tetrahedron:Asymm.* 5:1403 (1994); D. K. Robinson and K. Mosbach, *J. Chem. Soc. Chem. Commun.* 969 (1989)). These catalysts do not exhibit α-chymotrypsin-like hydrolytic activity, nor do they contain the functional groups namely imidazole, hydroxyl and carboxyl, involved in the active site of α-chymotrypsin.

OBJECTS OF THE INVENTION

Therefore, it is a principal object of the present invention to provide a new polymer composition that is useful for the conversion of esters and amides to the corresponding alcohols and amines and that overcomes the disadvantages inherent in the polymers hitherto used in the prior art.

Another object of the invention is to provide a process for the preparation of a polymer composition for the above-mentioned purpose that overcomes the limitations such as low reactivity and selectivity.

Yet another object of the present invention is to provide a process for the preparation of a polymer composition that offers additional advantages such as enhanced activity due to improved accessibility, stability at higher temperatures, ability to withstand pH variations, and enable switching on-off of the activity of the polymer in response to a particular stimulus especially light.

Another object of the invention is to provide a process for the conversion of esters and amides to the corresponding alcohols and amines that overcome the disadvantages inherent in the catalysts described in the prior art.

A further object of the present invention is to provide a process for the above-mentioned purposes that eliminate the difficulties associated with low reactivity, and problems associated with the recovery of enzyme catalysts from the reaction media and offer high catalytic activity and selectivity for the hydrolysis reactions.

SUMMARY OF THE INVENTION

The above objects are achieved with the present invention directed to a polymer composed of vinyl monomers bearing imidazole, hydroxyl and carboxyl groups arranged in proximity to each other as described below. The synthetic polymer exhibits hydrolytic activity similar to serine proteases, especially chymotrypsin, and is useful for the hydrolysis of esters and amides to their corresponding alcohols and amines. In addition, the invention provides a process for preparing the above-identified polymer composition.

DETAILED DESCRIPTION OF THE INVENTION

As a result of our sustained research, we have been able to ascertain that the catalytic activity of a hydrolytic polymer can be significantly enhanced when the functional groups present in the monomers are brought in close proximity by complexation in the presence of a metal ion and a print molecule and are immobilized by polymerization in the presence of a crosslinker on an inert support, such as the internal surface of macroporous polymer bead. This can be seen in Table 1 accompanying this specification.

In addition, we have also been able to ascertain that the conversion of the esters and amides to their corresponding alcohols and amines can be effected when carried out in the presence of a polymer prepared by a process described hereinbelow (See Examples 1–9).

Accordingly, the present invention provides a new polymer exhibiting hydrolytic activity similar to serine proteases, particularly chymotrypsin, which comprises a mixture of three monomers having the general formula: $A_x B_y C_z$, wherein A is a hydroxyl group-bearing vinyl monomer
B is a carboxyl group-bearing vinyl monomer, and
C is an imidazole group-bearing vinyl monomer, and x, y, z represent the molar concentration of each of the respective monomers such that $x+y+z=1$ and x, y can vary such that $0<x,y,x<1$.

The invention also provides a process of preparing a polymer exhibiting hydrolytic activity similar to serine proteases, especially chymotrypsin, and useful for the hydrolysis of esters and amides to the corresponding alcohols and amides, said process comprising:

(i) formation of a complex between a transition metal ion such as cobalt, nickel, manganese and copper, along with three vinyl monomers comprising a hydroxyl, a carboxyl and an imidazole group in the pendent chain, and a print molecule that has the size and shape (structure) similar to the ester or amide substrate to be hydrolyzed and has the ability to complex with the metal ion in a suitable solvent; and (ii) immobilizing the so-formed complex by polymerization in the presence of a crosslinker, and preferably a U.V. sensitive monomer, and polymerizing the resultant mixture preferably on an inert polymer support or with an excess hydrophilic monomer in the presence of a polymerization initiator.

A BRIEF DESCRIPTION OF THE DRAWINGS

Figure 1:
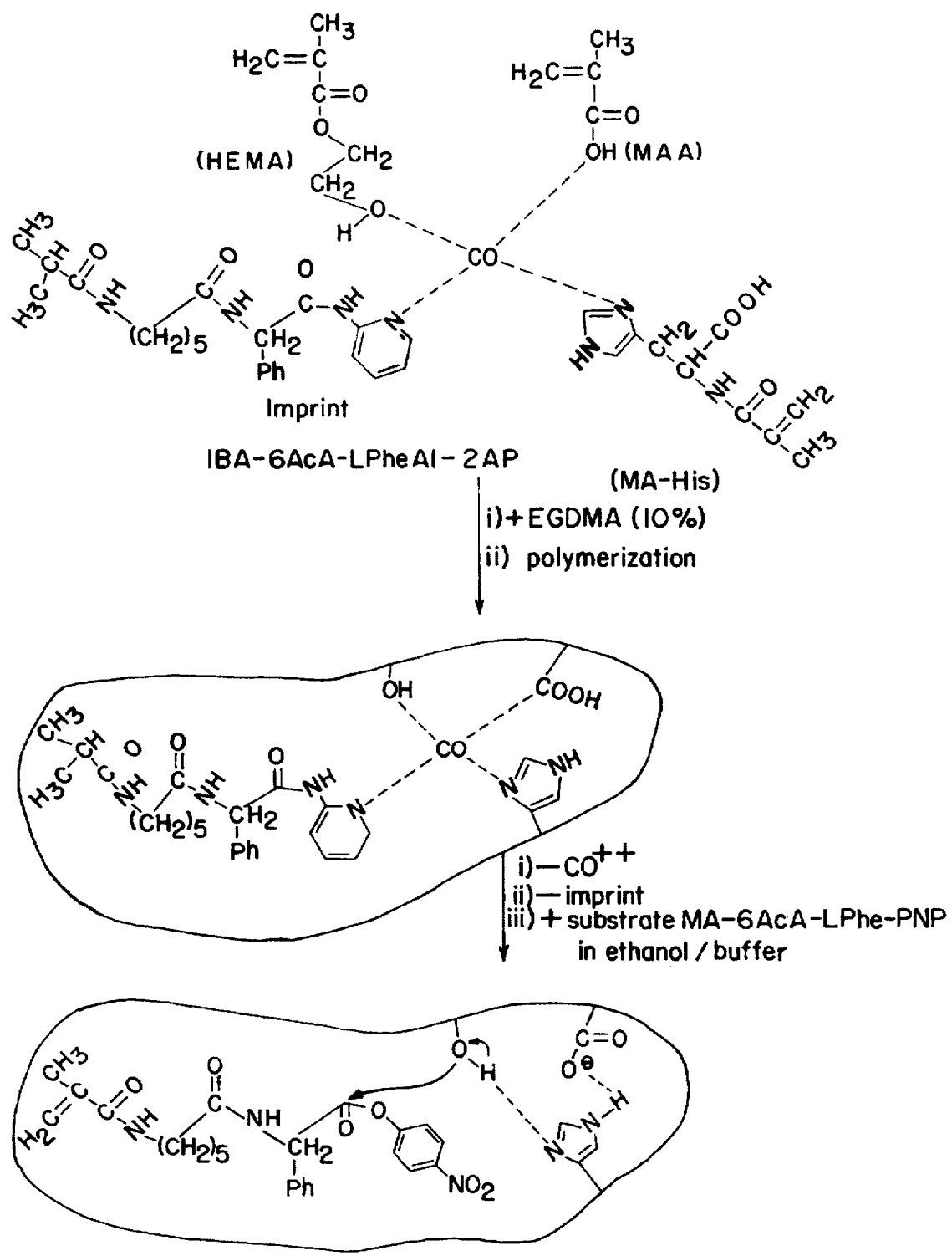
Figure 2:
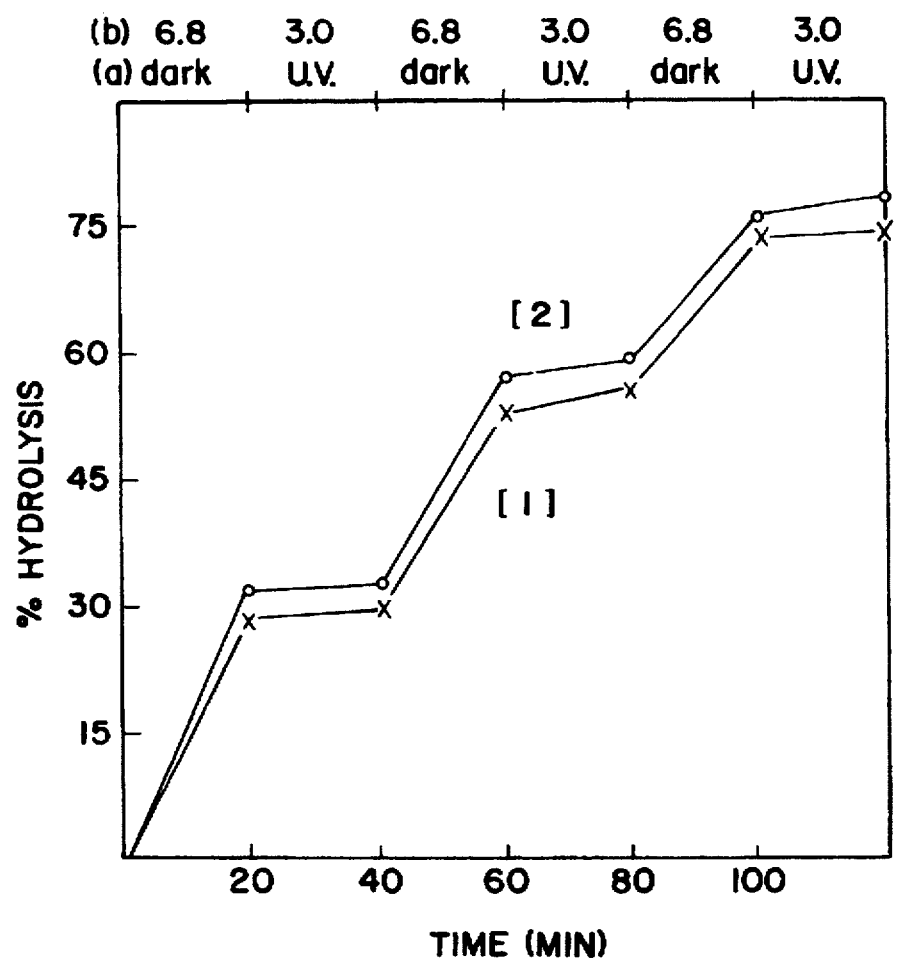

A typical reaction sequence of the present process is shown in FIG. 1 of the drawings accompanying the specification. FIG. 2 shows the percentage of p-nitrophenol released was plotted against time.

The polymer is formed by crosslinking and polymerization of the monomers around a print molecule that is structurally similar to the ester or amide substrate molecule to be hydrolyzed but will contain a pyridine group in place of the p-nitro group of the substrate molecule. The print molecule is structurally analogous to the substrate but contains a functional group (pyridine in this case) which can enter into complexation with the metal ion. Other groups that can be so used are amino, hydroxyl, carboxyl, and the like. After polymerization of the polymer on the inert support, the print molecule is leached out, leaving the polymer with the monomers positioned in proximity to each other according to the substrate molecule, and providing specific binding sites for the substrate molecule within the polymer.

The polymeric composition can be prepared, for example, in the form of discs, dense microspheres, or in the form of a thin film deposited on the internal surfaces of highly porous spherical beads. Such beads are generally prepared by the suspension polymerization of vinyl monomers such as glycidyl methacrylate, styrene and methyl methacrylate, in the presence of a diluent such as cyclohexanol. A typical procedure which can be used for the preparation of such beads is described by F. Svec, J. Coupek, and J. Kalal, *Angew. Makromol. Chem.* 48:135 (1975), the disclosure of which is incorporated by reference herein.

The functional monomers contained in the composition and used in the process have hydroxyl, carboxyl and imidazole groups linked to the vinyl group through the pendent link. Examples of the hydroxyl group-bearing vinyl monomer include 2-hydroxyethyl methacrylate, 2-hydroxypropyl methacrylate, p-styrene phenol, 2-hydroxyethyl methacrylamide, N-methacryloyl serine, methacryloyl 6-aminocaproyl serine, p-vinyl benzoyl 6-aminocaproyl serine, and the like. Examples of the imidazole group-bearing vinyl monomer include N-methacryloyl L-histidine, N-acrylcyl L-histidine, 4(5)vinyl imidazole, N-methacryloyl histamine, 6-aminocaproyl histidine, p-vinyl benzoyl 6-aminocaproyl histidine, and the like. Examples of the carboxyl group-bearing vinyl monomer include acrylic acid, methacrylic acid, N-methacryloyl 1-glutamic acid, N-methacryloyl aspartic acid, methacryloyl aspartic acid, p-vinyl benzoyl 6-aminocaproyl aspartic acid, and the like.

The metal ion used for complex formation can be chosen from the transition metal ions such as $Ni^{++}$, $Co^{++}$, $Zn^{++}$, $Cu^{++}$, $Fe^{+++}$, $Mg^{++}$, $Mn^{++}$, and similar transition metal ions. The print molecule can be synthesized according to known procedures in the art, for example, as described by A. Leonhardt and K. Mosbach, *React. Polym.* 6:287 (1985), the disclosure of which is incorporated by reference herein. Useful crosslinkers include, for example, ethylene glycol dimethacrylate, triethyleneglycol, dimethacrylate, divinyl benzene, trimethylol propane trimethacrylate, N,N' bisacrylamide, trimethylol propane acrylate, and the like. A preferred U.V. sensitive monomer is p-phenylazobenzoate. Examples of hydrophilic monomers useful in the polymerization include 2-hydroxyethyl methacrylate, 2-ethoxyethyl methacrylate, 2-hydroxypropyl methacrylate, and the like. The solvent used in the formation of the complex can be chosen from methanol, ethanol, propanol, butanol, acetonitrile, dichloromethane, dioxan, ethyl acetate, and the like.

The individual composition of the monomers and the print molecules in the complex can be varied. However, for the highest activity, a preferred composition of the hydroxyl-, imidazole-, and carboxyl-bearing vinyl monomers, the print molecule, and the metal ion is 1:1:1:1:1.

The polymerization temperature can be in the range of about 4°–40° C. for U.V. and $\Gamma$ irradiation, and about 55°–80° C. for thermal polymerization. Useful initiators for polymerization include azobisisobutyronitrile, t-butyl hydroperoxide, benzoyl peroxide, and the like. The period of polymerization employed can range from about 3–24 hours. The polymerization can be initiated thermally or by ultraviolet light in the presence of $\Gamma$ photoinitiator such as azobisisobutyronitrile or by $\Gamma$ irradiation. The inert atmosphere can be maintained using an inert gas such as nitrogen, argon, helium, neon, krypton, carbon dioxide, and the like. The polymerization of the complex can be carried out on the inner surface of a porous bead, as described, for example, by P. K. Dahl, S. Vidya Sankar, and F. H. Arnold, *Chem. Mater.* 7:154 (1995), the disclosure of which is incorporated by reference herein.

The inert polymer support used for the immobilization of the complex can be composed of a polymer such as poly (glycidyl methacrylate-ethyleneglycol dimethacrylate), poly (methylmethacrylate-ethyleneglycol dimethacrylate), poly (styrene-divinylbenzene), poly(trimethylol propane trimethacrylate-glycidyl methacrylate), poly(trimethyl propane triacrylate-glycidyl methacrylate), poly(trimethylol propane triacrylate-acrylenitrile), and the like. Preferably, the inert support is in the form of macroporous particles.

Examples of an initiator useful for thermal polymerization include azobisisobutyronitrile, t-butyl hydroperoxide, benzoyl peroxide, and the like. The period of polymerization employed may range from about 3–20 hours.

The metal ion can be extracted after polymerization is complete using a dilute acid such as an ethylenediamine tetraacetic acid solution, or by treating the polymers with a methanol solution containing 2,2'-bipyridyl or 1,10 phenanthroline. The surface area of the macroporous supports can be varied from about 50–800 m$^2$/g. The spheres can be in the size range of about 35–150μ.

The invention also provides a process for the conversion of a substrate containing ester or amide groups to the corresponding alcohol or amine, which comprises bringing the ester or amide substrate to be hydrolyzed in contact with a polymer composed of the hydroxyl, carboxyl and imidazole group-bearing monomers brought together in the vicinity of one another by complexation with a transition metal ion along with a print molecule, and immobilized on an inert support by polymerization in the presence of a crosslinking monomer. The hydrolysis is carried out at a temperature range of about 20°–80° C., and a pH range of about 6–11.

The polymer is brought in contact with the ester or amide substrate to be hydrolyzed, preferably in a mixed solvent system, at a temperature in the range of about 20°–80° C., in the presence or absence of U.V. light so as to bring about hydrolysis of the amide or alcohol until the reaction is complete.

The hydrolysis of the amide or ester substrate can be carried out in a mixed solvent system composed of, for example, an ethanol-buffer, acetonitrile-buffer, dioxane-buffer, and the like. The amount of the organic solvent in the polymer/substrate mixture can be in the range of about 10%–50%, with a preferable range being about 20–40%. The polymer catalyst to substrate ratio in the reaction can be varied from about 1:0.05 to about 1:50. The pH of the reaction mixture can be in the range of about pH 6–11, with a preferred range at about pH 7.5–8.0. The hydrolysis of amides or esters can be effected at a temperature range of about 20°–80° C., with a preferable range at about 25°–40° C.

The hydrolytic activity of the polymer depends, at least in part on the pH of the medium. The activity decreases with decreasing pH and almost completely disappears at pH below 3.5 because of the protonation of the imidazole group and suppression of the ionization of the carboxylic group. Also, by incorporating vinyl monomers that undergo cis-trans isomerism in response to U.V. irradiation, the hydrolysis of the esters and the amides can be controlled by external stimuli such as pH and U.V. irradiation.

The preparation of the polymer composition involves bringing together monomers comprising imidazole, hydroxyl and carboxyl groups along with a suitable imprinting/template in the presence of a metal ion. The complex that is formed is then adsorbed onto a microporous polymer support. This results in a highly porous structure on the surface of which are polymerized three monomers with their respective imidazole, hydroxyl and carboxyl functional groups positioned in the vicinity of each other, with the polymer structure being crosslinked by means of a crosslinker incorporated into the mixture during the polymerization stage. The metal ion and the print molecules are removed after polymerization is complete.

The ester or amide substrate to be hydrolyzed is not a part of the polymer composition. The substrate reacts with the polymer, resulting in the formation of a product with alcohol or amine groups. Since this is a true catalytic system, the ratio of moles of ester to moles of catalyst (polymer) used will be greater than one. In addition, when the complex is formed, the hydroxyl, carboxyl and imidazole bearing monomers and the imprints/templates are a part of the complex, and then polymerized. The hydroxyl group in the present invention is the nucleophile and its activity is enhanced by the presence of the carboxyl and imidazole groups.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references are incorporated by reference herein.

EXAMPLES

Example 1

0.286 gm (0.0022M) 2-hydroxyl ethyl methacrylate, 0.189 gm (0.0022M) methacrylic acid, 0.5 gm (0.0022M) N-methacrycoyl L-histidine and 0.932 gm (0.0022M) N-isobutyryl 6-amino caproyl L-phenyl alanyl 2-amino pyridine (imprint molecule) were placed in a 25 ml beaker. 5 ml methanol and 0.524 gm (0.0022M) $CoCl_2.6H_2O$ were added and the mixture was stirred for one hour at room temperature. Methanol was then evaporated under reduced pressure (5–50mm Hg) to give a deep blue coloured complex.

2.5 gm of this complex was placed in a glass test tube. To it, 2 gm 2-hydroxyethyl methacrylate, 0.5 ml ethylene glycol dimethacrylate and 0.8 ml t-butyl hydroperoxide were added. The test tube was purged with nitrogen for 10 minutes and then immersed in a water bath maintained at 65° C. The polymerization was carried out for 16 hours. The polymer was isolated in the form of a cylindrical rod by breaking the test tube. The rod was then cut into discs of 0.09–11 cm thickness on a lathe. The yield obtained was 4 gm.

These discs were dipped into a 1% 2,2'-bipyridyl solution in methanol for 12 hours to remove $Co^{++}$ and the imprint molecule. The solution of 2,2'-bipyridyl was changed after every 4 hours. Further, the discs were washed with dilute HCl and dried in a vacuum oven at room temperature for 48 hours.

The substrate N-methacryloyl 6-aminocaproyl L-phenylalanyl p-nitrophenol was sorbed into the discs from an acetone solution. It was then polymerized by exposing the discs to Γ irradiation from a $Co^{60}$ source of 0.25 Mrad/hr for 6 hours. The unreacted monomer was extracted in acetone.

The concentration of the catalytic groups based on the moles of imidazole was $2\times10^5$M/gm of polymer. Disc weighing 0.12 gm was suspended in 50 ml ethanol/phosphate buffer (0.01M, pH 8) in the ratio 40:60 v/v maintained at 37° C. Stock solution of the substrate N-methacryloyl 6-aminocaproyl L-phenylalanyl p-nitrophenol was prepared in dry ethanol (0.024M/lit). 10 μl of the substrate was added and the hydrolysis of the ester was monitored by the amount of p-nitrophenol released in the medium, by U.V. spectrophotometer at 400 nm. After 8 hours, 95% of the substrate was converted to p-nitro phenol.

Example 2

0.286 gm (0.0022M) 2-hydroxyethyl methacrylate, 0.189 gm (0.0022M) methacrylic acid, 0.5 gm (0.0022M) N-methacryloyl L-histidine, 0.932 gm (0.0022M) isobutyryl 6-amino caproyl L-phenylalanine 2-aminopyridine were mixed well in 5 ml methanol in a 25-ml beaker. 0.524 gm (0.0022M) $CoCl_2.6H_2O$ was added and the solution was stirred for 1 hour at room temperature to give a blue coloured complex. Methanol was evaporated under reduced pressure. 2 gm 2-hydroxyethyl methacrylate, 0.3 ml ethylene glycol dimethacrylate and 0.030 gm AIBN were further added to the mixture and air was expelled from the mixture using nitrogen. In a three-necked round bottom flask equipped with a stirrer, 47 ml 35% NaCl solution was added. To this, 3 ml 1N NaOH and 2 gm $MgCl_2.6H_2O$ were added to give a uniform suspension of $Mg(OH)_2$. A stream of nitrogen was passed through the solution for 15 minutes. The monomer mixture was added dropwise to the suspension and stirred at 1000 rpm at 75° C. for 3 hours. The monomer mixture was dispersed into fine droplets which were then polymerized into rigid spheres. The spheres were isolated by filtration. The yield obtained was 3.8 gm.

The microspheres were subjected to repeated extraction with 1% methanolic solution of 2,2'-bipyridyl and dilute HCl, followed by drying in a vacuum oven at room temperature for 48 hours.

The concentration of the catalytic groups based on the number of moles of imidazole was found to be $2.5 \times 10^{-5}$M/gm. 50 mg of the polymer was taken in 25 ml solution of ethanol/phosphate buffer (0.01M, pH 8) in 40:60 vol/vol. The temperature was maintained at 37° C. 25 ml of the above reaction mixture was placed in another flask. 2.5 mg α-chymotrypsin was added. A stock solution of the substrate N-methacryloyl L-phenyl alanyl p-nitrophenol was prepared in dry ethanol (0.0012M/lit). 10 μl of this was added simultaneously to the flasks containing the polymeric catalyst and the native enzyme, respectively. The reaction was followed by the amount of p-nitrophenol released in the reaction medium. After 20 minutes, 90% of the substrate was converted into product by the enzyme and 60% by the polymeric catalyst.

Example 3

0.286 gm (0.0022M) 2-hydroxyethyl methacrylate, 0.189 gm (0.0022M) methacrylic acid, 0.5 gm (0.0022M) N-methacryloyl L-histidine and 0.932 gm (0.0022M) isobutyryl 6-aminocaproyl-L-phenylalanine-2-amino pyridine were mixed together in 5 ml methanol. 0.524 gm (0.0022M) $CoCl_2.6H_2O$ was added and stirred well for one hour to give a blue complex. Methanol was evaporated under reduced pressure.

Further, 0.3 gm 2-methacryloyl hydroxyethyl p-phenyl azobenzoate, 1.7 gm 2-hydroxyethyl methacrylate, 0.3 ml ethyleneglycol dimethacrylate, and 0.030 gm azobisisobutyronitrile were added, and the mixture was purged with nitrogen for 10 minutes.

In a three-necked round bottom flask equipped with a stirrer, 47 ml 35% NaCl solution was added. To this, 3 ml 1N NaOH and 2 gm $MgCl_2.6H_2O$ were added to give a uniform suspension of $Mg(OH)_2$. This mixture was purged with nitrogen for 15 minutes. The monomer mixture was added dropwise to the $Mg(OH)_2$ suspension. The temperature was maintained at 75° C. and the mixture was stirred at 1000 rpm for 3 hours. Spheres were isolated by filtration. The yield obtained was 3.5 gm.

The spheres were subjected to repeated extraction with 1% 2,2'-bipyridyl solution in methanol and then with dilute HCl for 12 hours, followed by drying in vacuum oven at room temperature for 48 hours.

The catalytic group concentration was found to be $2.5 \times 10^5$M/gm. 50 mg of the catalyst was placed in a 25 ml flask which was constantly stirred. The flask was covered with layers of aluminum foil to protect against light. 100 μl of the substrate solution (0.00012M/lit) was added and the hydrolysis was allowed to take place for 20 minutes at 30° in darkness. (The substrate solution, the same as in Example 2, was prepared by dissolving the substrate N-methacryloyl L-phenyl alanyl p-nitrophenol in dry ethanol.) The amount of p-nitrophenol formed was measured at 400 nm. Immediately, the flask was exposed to U.V. light of 280–350 nm for the next 20 minutes. This cycle was repeated five times. The percentage of p-nitrophenol within a specified time period when the microspheres are exposed alternately to 280–350 nm U.V. light is summarized in Table 2 accompanying this specification. The percentage of p-nitrophenol released was plotted against time, as shown in FIG. 2 of the drawings accompanying the specification.

Example 4

0.286 gm (0.0022M) 2-hydroxyethyl methacrylate, 0.189 gm (0.0022M) methacrylic acid, 0.5 gm (0.0022M) N-methacryloyl L-histidine, and 0.932 gm (0.0022M) isobutyryl 6-aminocaproyl-L-phenylalanine-2-amino pyridine were mixed together in 5 ml methanol. 0.524 gm (0.0022M) $CoCl_2.6H_2O$ was added and stirred well for one hour to give a blue complex. Methanol was evaporated under reduced pressure. Further, 0.3 gm 2-methacryloyl hydroxyethyl p-phenyl azobenzoate, 1.7 gm 2-hydroxyethyl methacrylate, 0.3 ml ethyleneglycol dimethacrylate, and 0.030 gm azobisisobutyronitrile were added, and the mixture was purged with nitrogen for 10 minutes.

In a three-necked round bottom flask equipped with a stirrer, 47 ml 35% NaCl solution was added. To this, 3 ml 1N NaOH and 2 gm $MgCl_2.6H_2O$ were added to give a uniform suspension of $Mg(OH)_2$. This mixture was purged with nitrogen for 15 minutes. The monomer mixture was added dropwise to the $Mg(OH)_2$ suspension. The temperature was maintained at 75° C. and the mixture was stirred at 1000 rpm for 3 hours. Spheres were isolated by filtration. The yield obtained was 3.5 gm.

The spheres were subjected to repeated extraction with 1% 2,2'-bipyridyl solution in methanol and then with dilute HCl for 12 hours, followed by drying in a vacuum oven at room temperature for 48 hours.

The catalytic group concentration was found to be $2.5 \times 10^5$M/gm. Two conical flasks containing 25 ml ethanol/phosphate buffer (pH 6.8) and ethanol/citrate buffer (pH 3) were stirred at 37° C. 50 mg polymer catalyst was added to the buffer of pH 6.8. 100 μl of the substrate stock solution as described in Example 2 above, was added and the reaction was monitored for 20 minutes. After 20 minutes, the medium was decanted and the catalyst was transferred to the flask containing buffer of pH 3 for the next 20 minutes. The percentage of p-nitrophenol released within a specified time period when exposed to different pH media is summarized in Table 3 accompanying this specification.

Example 5

3.6 gm of glycidyl methacrylate, 8.4 gm ethylene glycol dimethacrylate, and 0.120 gm azobisisobutyronitrile were mixed with 16 gm cyclohexanol and suspended into a solution of 88 ml 1% polyvinylpyrrolidone (M.W. $3.6 \times 10^5$) in a 100-ml round bottom flask. Air was expelled from the reaction vessel by a stream of nitrogen. The stirring rate was adjusted to 1000 rpm and the polymerization was performed at 70° C. for 2 hours and at 80° C. for 6 hours. The mixture was allowed to cool for 2 hours. The spheres were isolated by filtration and washed with water and alcohol repeatedly and dried in a vacuum oven at 40° C. for 48 hours. Spheres in the size range 37°–45μ were chosen. 0.286 gm (0.0022M) 2-hydroxyethyl methacrylate, 0.189 gm (0.0022M) methacrylic acid, 0.5 gm (0.0022M) N-methacryloyl L-histidine, 0.932 gm (0.0022M) isobutyryl 6-aminocaproyl-L-phenylalanine-2-aminopyridine, 0.1 ml ethylene glycol dimethacrylate, 0.524 gm (0.0022M) $CoCl_2.6H_2O$ and 0.1 gm azobisisobutyronitrile were mixed together in 5 ml methanol. 1 gm macroporous spheres were added to this and stirred for 24 hours and filtered. The monomer mixture that was adsorbed on the internal surface of the spheres was then polymerized thermally at 75° C. for 24 hours.

The spheres were subjected to repeated extraction with methanolic solution of 2,2'-bipyridyl and dilute HCl followed by drying in a vacuum oven at room temperature for 48 hours.

The catalytic group concentration in the surface imprinted polymer was found to be $2.1 \times 10^4$ M/gm. 50 mg of the catalyst was suspended in 25 ml of ethanol/phosphate buffer (0.01M, pH 8) in the ratio 40:60 vol/vol. Stock solution of the substrates N-methacryloyl 6-amino-caproyl L-phenylalanyl p-nitrophenol, and N-methacryloyl 6-aminocaproly L-phenyl alanyl p-nitroanilide, were prepared in dry ethanol (0.0021M/lit). 100 µl of the substrate stock solution was added to the three conical flasks. The amount of p-nitrophenol and p-nitroaniline released was monitored spectrophotometrically at 400 nm and 380 nm respectively to follow the course of the reaction. Identical experiments were also carried out using α-chymotrypsin (5.25 mg/25ml of the reaction medium) as the catalyst. After 20 minutes, 100% of N-methacryloyl 6-amino caproyl L-phenylalanyl p-nitrophenol was converted to the product by the polymer catalyst while 90% conversion was observed for the enzyme. For the amide substrate, after 30 minutes the conversion was 65% in the presence of the enzyme and 43% in the presence of the polymeric catalyst.

Example 6

0.286 gm (0.0022M) 2-hydroxyethyl methacrylate, 0.189 gm (0.0022M) methacrylic acid, 0.5 gm (0.0022M) N-methacryloyl L-histidine, 0.932 gm (0.0022M) isobutyryl 6-amino caproyl L-phenylalanine 2-amino pyridine were mixed well in 5 ml methanol in a 25-ml beaker. 0.524 gm (0.0022M) $CoCl_2.6H_2O$ was added and the solution was stirred for 1 hour at room temperature to give a blue colored complex. Methanol was evaporated under reduced pressure. 2 gm 2-hydroxyethyl methacrylate, 0.3 ml ethylene glycol dimethacrylate, and 0.030 gm azobisisobutyronitrile were further added to the mixture and air was expelled from the mixture using nitrogen. In a three-necked round bottom flask equipped with a stirrer, 47 ml 350 NaCl solution was added. To this, 3 ml 1N NaOH and 2 gm $MgCl_2.6H_2O$ were added to give a uniform suspension of $Mg(OH)_2$. A stream of nitrogen was passed through the solution for 15 minutes. The monomer mixture was added dropwise to the suspension and stirred at 1000 rpm at 75° C. for 3 hours. The monomer mixture was dispersed into fine droplets which were then polymerized into rigid spheres. The spheres were isolated by filtration. The yield obtained was 3.8 gm.

The microspheres were subjected to repeated extraction with 1% methanolic solution of 2,2'-bipyridyl and dilute HCl, followed by drying in a vacuum oven at room temperature for 48 hours.

The concentration of the catalytic groups based on the number of moles of imidazole was found to be $2.5 \times 10^{-5}$M/ gm. 50 mg of the polymer catalyst was exposed to a thermal shock at 75° C. for 2 hours in an oven. After cooling the polymer catalyst to 25° C., the hydrolysis of N-methacryloyl 6-aminocaproyl L-phenylalanyl p-nitrophenol was followed in 25 ml ethanol/phosphate buffer (0.01M, pH 8) at 37° C. After 20 minutes, 60% of the substrate was converted to p-nitrophenol. When the catalyst was not subjected to higher temperatures, the conversion under identical conditions was also 60% indicating that the stability of the catalyst was not affected by exposure to higher temperatures.

Example 7

0.286 gm (0.0022M) 2-hydroxyethyl methacrylate, 0.189 gm (0.0022M) methacrylic acid, 0.5 gm (0.0022M) N-methacryloyl L-histidine, 0.932 gm (0.0022M) isobutyryl 6-amino caproyl L-phenylalanine 2-amino pyridine were mixed well in 5 ml methanol in a 25 ml beaker. 0.524 gm (0.0022 M) $CoCl_2.6H_2O$ was added and the solution was stirred for 1 hour at room temperature to give a blue colored complex. Methanol was evaporated under reduced pressure. 2 gm 2-hydroxyethyl methacrylate, 0.3 ml ethylene glycol dimethacrylate, and 0.030 gm azobisisobutyronitrile were further added to the mixture and air was expelled from the mixture using nitrogen. In a three-necked round bottom flask equipped with a stirrer, 47 ml 35% NaCl solution was added. To this, 3 ml 1N NaOH and 2 gm $MgCl_2.6H_2O$ were added to give a uniform suspension of $Mg(OH)_2$. A stream of nitrogen was passed through the solution for 15 minutes. The monomer mixture was added dropwise to the suspension and stirred at 1000 rpm at 75° C. for 3 hours. The monomer mixture was dispersed into fine droplets which were then polymerized into rigid spheres. The spheres were isolated by filtration. The yield obtained was 3.8 gm.

The microspheres were subjected to repeated extraction with 1% methanolic solution of 2,2'-bipyridyl and dilute HCl, followed by drying in a vacuum oven at room temperature for 48 hours.

The concentration of the catalytic groups based on the number of moles of imidazole was found to be $2.5 \times 10^{-5}$ M/gm. 50 mg of the catalyst used to hydrolyze $1.25 \times 10^6$M/ lit of N-methacryloyl 6-aminocaproyl L-phenylalanyl p-nitrophenol repeatedly. After all the ester was converted to p-nitrophenol, the spheres were washed with phosphate buffer of pH 8 for 1 hour and dried in a vacuum oven at room temperature. Again a fresh solution of the ester was added. This procedure was repeated 45 times with the same catalyst. The catalytic activity was determined by the percentage of substrate that was converted into product by the polymeric catalyst each time. It was observed that the activity of the polymeric catalyst was retained within 98% of the original after 20 recycles and within 95% after 45 recycles as seen in Table 4 accompanying this specification.

Example 8

3.6 gm of glycidyl methacrylate, 8.4 gm ethylene glycol dimethacrylate and 0.120 gm azobisisobutyronitrile were mixed with 16 gm cyclohexanol and suspended into a solution of 88 ml 1% polyvinylpyrrolidone (M.W. $3.6 \times 10^5$) in a 100 ml round bottom flask. Air was expelled from the reaction vessel by a stream of nitrogen. Stirring rate was adjusted to 1000 rpm and the polymerization was performed at 70° C. for 2 hours and at 80° C. for 6 hours. The mixture was allowed to cool for 2 hours. The spheres were isolated by filtration and washed with water and alcohol repeatedly and dried in a vacuum oven at 40° C. for 48 hours. Spheres in the size range 37–45µ were chosen.

0.286 gm (0.0022M) 2-hydroxyethyl methacrylate, 0.189 gm (0.0022M) methacrylic acid, 0.5 gm (0.0022M) N-methacryloyl L-histidine, 0.932 gm (0.0022M) isobutyryl 6-aminocaproyl-L-phenylalanine-2-aminopyridine, 0.1 ml ethylene glycol dimethacrylate, 0.524 gm (0.0022M) $CoCl_2.6H_2O$ and 0.1 gm azobisisobutyronitrile were mixed together in 5 ml methanol. 1 gm of macroporous spheres were added to this and stirred for 24 hours and filtered. The monomer mixture that was absorbed on the internal surface of the spheres was then polymerized thermally at 75° C. for 24 hours.

The spheres were subjected to repeated extraction with methanolic solution of 2,2'-bipyridyl and dilute HCl followed by drying in vacuum oven at room temperature for 48 hours.

The catalytic group concentration in the surface imprinted polymer was found to be $2.1 \times 10^{-4}$ M/gm. 50 mg of polymer catalyst was exposed to alkaline media (pH 11) at room temperature for 2 hours. The spheres were washed thoroughly with distilled water to remove all traces of alkali. The catalyst was suspended in 25 ml of ethanol/phosphate buffer (0.01 M, pH 8) in the ratio 40:60 vol/vol. A stock solution of the substrate N-methacryloyl 6-amino caproyl L-phenylalanyl p-nitrophenol was prepared in dry ethanol (0.0021M/lit). 100 μl of the substrate stock solution was added to the conical flask. The amount of p-nitrophenol released was monitored spectrophotometrically at 400 nm to follow the course of the reaction. 98% of N-methacryloyl 6-amino caproyl L-phenylalanyl p-nitrophenol was converted to the product by the polymer catalyst. The activity of the catalyst was retained within 98% of the original.

Example 9

The complex comprising 2-hydroxyethyl methacrylate (0.0022M), methacrylic acid (0.0022M), N-methacryloyl L-histidine (0.0022 M), and $CoCl_2 \cdot 6H_2O$ (0.0022M), with 0.1 ml ethylene glycol dimethacrylate and 0.1 gm azobisisobutyronitrile, was absorbed on the surface of 1 gm of poly(glycidyl methacrylate-ethylene glycol dimethacrylate) microspheres for 24 hours and filtered. The polymerization was initiated by U.V. light at 4° C. for 6 hours. The spheres were subjected to repeated extraction with 1% 2,2'-bipyridyl solution in methanol and with dilute HCl followed by drying in a vacuum oven at room temperature for 48 hours.

The active site concentration based on the imidazole was $1.8 \times 10^6$ M/gm. 50 mg of the catalyst was suspended in 25 ml of ethanol/buffer in the ratio 40:60 v/v. A stock solution of the substrate N-methacryloyl 6-aminocaproyl D-phenylalanyl p-nitrophenol was prepared. 100 μl of the substrate was added and the hydrolysis was followed by the release of p-nitrophenol. It was observed that after 20 minutes only 56% of N-methacryloyl 6-aminocaproyl D-phenylalanyl p-nitrophenol was converted to the p-nitrophenol. Conversion for the L-isomer was 100% indicating the selective nature of the polymeric catalyst.

TABLE 1

Comparative study of the hydrolytic activity of different polymeric catalysts and the enzyme

| Catalyst | Substrate | Time | % Hydrolysis |
| --- | --- | --- | --- |
| Dense microspheres prepared using im printing (37–45 μ) | MA-6ACA-L-PheAl-PNP | 20 min. | 60 |
| Dense microspheres prepared without imprinting | MA-6ACA-L-PheAl-PNP | 20 min. | 21 |
| Porous high surface area imprinted catalyst | MA-6ACA-L-PheAl-PNP | 12 min. | 90 |
| Porous high surface area catalyst without imprinting | MA-6ACA-L-PheAl-PNP | 12 min. | 15 |
| α-chymotrypsin | MA-6ACA-L-PheAl-PNA | 12 min. | 70 |
| Porous high surface area imprinted catalyst | MA-6ACA-L-PheAl-PNA | 30 min. | 43 |
| Porous high surface area catalyst without imprinting | MA-6ACA-L-PheAl-PNA | 30 min. | 8 |

TABLE 2

On/off hydrolytic activity of the polymeric catalyst when exposed alternately to U.V.

| Time (min.) | Presence or absence of U.V. | % Hydrolyzed |
| --- | --- | --- |
| 20 | darkness | 27 |
| 40 | U.V. ($\lambda_{max}$ = 280–350 nm) | 2 |
| 60 | darkness | 24 |
| 80 | U.V. ($\lambda_{max}$ = 280–350 nm) | 3 |
| 100 | darkness | 15 |
| 120 | U.V. ($\lambda_{max}$ = 280–350 nm) | 2.5 |

TABLE 3 pH-sensitive hydrolytic activity of the polymeric catalyst for ester hydrolysis

| Time (min.) | pH of the reaction medium | % Hydrolysis |
| --- | --- | --- |
| 20 | 6.8 | 33 |
| 40 | 3.0 | 1 |
| 60 | 6.8 | 20 |
| 80 | 3.0 | 2 |
| 100 | 6.8 | 17 |
| 120 | 3.0 | 3 |

TABLE 4

Repeated use of the surface imprinted polymer catalyst for the hydrolysis of ester

| No. of cycles | Catalytic Activity of the polymeric catalyst % of the virgin catalyst |
| --- | --- |
| 5 | 99.98 |
| 10 | 99.54 |
| 15 | 99.09 |
| 20 | 98.87 |
| 25 | 97.84 |
| 30 | 97.42 |
| 35 | 97.06 |
| 40 | 96.86 |
| 45 | 95.80 |

We claim:

1. A synthetic polymer which can hydrolyze a substrate containing an ester or amide group to the corresponding alcohol or amine; the polymer having the general formula $A_x B_y C_z$, wherein A is a vinyl monomer containing a hydroxyl group, B is a vinyl monomer containing a carboxyl group, and C is a vinyl monomer containing an imidazole group; and x, y, z represent the mole fraction of each of the respective monomers wherein x+y+z=1 and x,y can vary such that 0<x,y z<1;

the vinyl monomers A, B and C being adjacent to each other by complexation with a transition metal ion and polymerization with a crosslinking monomer, wherein the polymer will selectively bind with and hydrolyze the substrate.

2. The polymer according to claim 1, wherein the hydroxyl group-bearing monomer is selected from the group consisting of 2-hydroxyethyl methacrylate, 2-hydroxypropyl methacrylate, p-styrene phenol, N-methacryloyl serine, 2-hydroxyethyl methacrylamide, N-methacryloyl serine, methacryloyl 6-aminocaproyl serine, and p-vinyl benzoyl 6-aminocaproyl serine.

3. The polymer according to claim 1, wherein the imidazole group-bearing monomer is selected from the group consisting of N-methacryloyl L-histidine, N-acryloyl L-histidine, 4(5)vinyl imidazole, N-methacryloyl histamine, methacryloyl 6-aminocaproyl histidine, and p-vinyl benzoyl 6-aminocaproyl histidine.

4. The polymer according to claim 1, wherein the carboxyl group-bearing monomer is selected from the group consisting of acrylic acid, methacrylic acid, N-methacryloyl L-glutamic acid, N-methacryloyl aspartic acid, methacryloyl 6-aminoaproyl aspartic acid, and p-vinyl benzoyl 6-aminocaproyl aspartic acid.

5. A process of preparing a polymer which can hydrolyze a substrate containing an ester or amide group to the corresponding alcohol or amide group, comprising:

(a) forming a complex between a transition metal ion, a vinyl monomer with a hydroxyl group in the pedant chain, a vinyl monomer with a carboxyl group in the pendent chain, and a vinyl monomer with an imidazole group in the pendent chain, and a print molecule having a size and structure similar to the ester or amide substrate to be hydrolyzed and which can complex with the metal ion; and (b) immobilizing the complex on an inert support by polymerizing the vinyl monomers in the presence of a crosslinking monomer.

6. The process according to claim 5, wherein the monomers are polymerized in step (b) in the presence of a monomer that is sensitive to U.V. light.

7. The process according to claim 5, wherein the polymerization is carried out at a temperature of about 55°–80° C., in the presence of a thermal initiator.

8. The process according to claim 5, wherein the polymerization is carried out at a temperature of about 4°–40° C., in the presence of the U.V. sensitive initiator, and initiated by U.V. irradiation.

9. The process according to claim 5, wherein at least one of the vinyl monomers contains the hydroxyl, carboxyl, or imidazole group as a terminal group in the pendent chain.

10. The process according to claim 5, wherein the hydroxyl group-bearing vinyl monomer is selected from the group consisting of 2-hydroxyethyl methacrylate, 2-hydroxypropyl methacrylate, p-styrene phenol, N-methacryloyl serine, 2-hydroxyethyl methacrylamide, N-methacryloyl serine, methacryloyl 6-aminocaproyl serine, and p-vinyl benzoyl 6-aminocaproyl serine.

11. The process according to claim 5, wherein the imidazole group-bearing vinyl monomer is selected from the group consisting of N-methacryloyl L-histidine, N-acryloyl L-histidine, 4(5)vinyl imidazole, N-methacryloyl histamine, methacryloyl 6-aminocaproyl histidine, and p-vinyl benzoyl 6-aminocaproyl histidine.

12. The process according to claim 5, wherein the carboxyl group-bearing vinyl monomer is selected from the group consisting of acrylic acid, methacrylic acid, N-methacryloyl L-glutamic acid, N-methacryloyl aspartic acid, methacryloyl 6-aminoaproyl aspartic acid, and p-vinyl benzoyl 6-aminocaproyl aspartic acid.

13. The process according to claim 5, wherein the metal ion is selected from the group consisting of $Ni^{++}$, $Co^{++}$ $Zn^{++}$, $Cu^{++}$, $Mg^{++}$, $Mn^{++}$, and $Fe^{+++}$.

14. The process according to claim 5, wherein the complex is formed in a solvent selected from the group consisting of ethanol, methanol, propanol, butanol, acetonitrile, ethyl acetate, dioxin, and dichloromethane.

15. The process according to claim 5, wherein the crosslinking monomer is selected from the group consisting of ethylene glycol dimethacrylate, triethyleneglycol, dimethacrylate, divinyl benzene, trimethylol propane trimethacrylate, N,N' bisacrylamide, and trimethylol propane acrylate.

16. The process according to claim 5, wherein the polymerization is at a temperature of about 4°–40° C. for U.V. and $\Gamma$ irradiation polymerization, or about 55°–75° C. for thermal polymerization.

17. The process according to claim 5, wherein the polymerization is carrier out in an inert atmosphere that is maintained by using an inert gas.

18. The process according to claim 5, wherein the inert support in step b) is composed of a polymer selected from the group consisting of poly(glycidyl methacrylate ethyleneglycol dimethacrylate), poly(methyl-methacrylate ethyleneglycol dimethacrylate), poly(styrene-divinylbenzene), poly(trimethylol propane trimethacrylate-glycidyl methacrylate), poly(trimethylol propane trimethacrylate-acrylonitrile), poly(trimethylol propane triacrylate-glycidyl methacrylate), and poly(trimethylol propane triacrylate-acrylonitrile).

19. The process according to claim 7, wherein the thermal initiator is selected from the group consisting of azobisisobutyronitrile, t-butyl hydroperoxide, and benzoyl peroxide.

20. A process for the hydrolysis of a substrate containing an ester or amide group to the corresponding alcohol or amine, comprising:

(a) mixing the substrate to be hydrolyzed with a polymer comprising a hydroxyl, carboxyl and imidazole group-bearing vinyl monomer positioned adjacent to each other by complexation with a transition metal ion and a print molecule; and (b) immobilizing the polymer on an inert support by polymerization of the vinyl monomers in the presence of a crosslinking monomer; and (c) contacting the substrate with the immobilized polymer wherein the hydrolysis is carried out a temperature of about 20°–80° C. and a pH of about 6–11.

21. The process according to claim 20, wherein the ratio of the hydroxyl group-bearing vinyl monomer:imidazole group-bearing vinyl monomer:carboxyl group-bearing vinyl monomer:print molecule:metal ion is about 1:1:1:1:1.

22. The process according to claim 20, wherein at least one of the vinyl monomers contains the hydroxyl, carboxyl or imidazole group as a terminal group in the pendent chain.

23. The process according to claim 20, wherein the hydroxyl group-bearing vinyl monomer is selected from the group consisting of 2-hydroxyethyl methacrylate, 2-hydroxypropyl methacrylate, p-styrene phenol, N-methacryloyl serine, 2-hydroxyethyl methacrylamide, N-methacryloyl serine, methacryloyl 6-aminocaproyl serine, and p-vinyl benzoyl 6-aminocaproyl serine.

24. The process according to claim 20, wherein the imidazole group-bearing vinyl monomer is selected from the group consisting of N-methacryloyl L-histidine, N-acryloyl L-histidine, 4(5)-vinyl imidazole, N-methacryloyl histamine methacryloyl 6-aminocaproyl histidine, and p-vinyl benzoyl 6-aminocaproyl histidine.

25. The process according to claim 20, wherein the carboxyl group-bearing vinyl monomer is selected from the group consisting of acrylic acid, methacrylic acid, N-methacryloyl L-glutamic acid, N-methacryloyl aspartic acid, methacryloyl 6-aminocaproyl aspartic acid, and p-vinyl benzoyl 6-aminocaproyl aspartic acid.

26. The process according to claim 20, wherein the hydrolysis is carried out in a mixed solvent system selected from an ethanol-buffer, acetonitrile-buffer, and dioxane-buffer.

27. The process according to claim 20, wherein the hydrolysis is carrier out in a solvent and the concentration of the solvent in the substrate and polymer mixture is about 10–50%.

28. The process according to claim 20, wherein the molar ratio of the polymer to the ester or amide being hydrolyzed is about 1:0.05 to 1:50.

29. The process according to claim 20, wherein the pH in step c) is about pH 7.5–8.

* * * * *